United States Patent
Haimerl et al.

(10) Patent No.: US 9,095,375 B2
(45) Date of Patent: Aug. 4, 2015

(54) METHOD FOR PLANNING POSITIONING OF A BALL JOINT PROSTHESIS

(75) Inventors: Martin Haimerl, Gilching (DE); Lars Dohmen, Munich (DE); Melanie Wegner, Kirchseeon (DE); Sabine Gneiting, Taufkirchen (DE)

(73) Assignee: Brainlab AG, Feldkirchen (DE)

( * ) Notice: Subject to any disclaimer, the term of this patent is extended or adjusted under 35 U.S.C. 154(b) by 65 days.

(21) Appl. No.: 13/992,391

(22) PCT Filed: Jan. 20, 2011

(86) PCT No.: PCT/EP2011/050735
§ 371 (c)(1), (2), (4) Date: Jun. 7, 2013

(87) PCT Pub. No.: WO2012/097873
PCT Pub. Date: Jul. 26, 2012

(65) Prior Publication Data
US 2013/0261760 A1    Oct. 3, 2013

(51) Int. Cl.
*A61B 19/00* (2006.01)
*A61F 2/32* (2006.01)

(52) U.S. Cl.
CPC ............. *A61B 19/50* (2013.01); *A61B 19/5244* (2013.01); *A61F 2/32* (2013.01); *A61B 2019/504* (2013.01)

(58) Field of Classification Search
CPC ....... A61F 2/46; A61F 2/32; A61B 2019/507; A61B 2019/502; A61B 2019/504; A61B 19/50
USPC .......................................................... 606/91
See application file for complete search history.

(56) References Cited

U.S. PATENT DOCUMENTS

| 5,880,976 A | 3/1999 | DiGioia, III et al. |
| 6,205,411 B1 | 3/2001 | Digioia, III et al. |
| 2004/0102866 A1* | 5/2004 | Harris et al. ................... 700/117 |
| 2004/0230199 A1* | 11/2004 | Jansen et al. .................... 606/91 |

(Continued)

FOREIGN PATENT DOCUMENTS

WO    2006/133806 A1    12/2006

OTHER PUBLICATIONS

International Search Report for International Application No. PCT/EP2011/050735 dated Oct. 7, 2011.

*Primary Examiner* — Sean Dougherty
*Assistant Examiner* — Michael C Stout
(74) *Attorney, Agent, or Firm* — Tucker Ellis LLP

(57) ABSTRACT

The present invention relates to a method for planning the positioning of a ball joint prosthesis, in particular a hip joint prosthesis, wherein the prosthesis includes a stem and a cup and the method comprises the following steps: —determining the position of at least one point lying on the rim of the joint socket, in particular the position of at least two points lying in an anterior region of the acetabulum; —defining a requirement for the position and/or orientation of the cup on the basis of the determined positions of the at least one point. The present invention also relates to a method for optimizing the positioning of a ball joint prosthesis, in particular a hip joint prosthesis, wherein the prosthesis includes a stem and a cup and the method comprises the following steps: —defining at least one requirement for the position and/or orientation of the cup; —calculating an optimum position and/or orientation of the cup on the basis of all the defined requirements being fulfilled.

19 Claims, 2 Drawing Sheets

(56) References Cited

U.S. PATENT DOCUMENTS

| | | |
|---|---|---|
| 2005/0203536 A1 | 9/2005 | Laffargue et al. |
| 2006/0241405 A1 | 10/2006 | Leitner et al. |
| 2007/0066917 A1 | 3/2007 | Hodorek et al. |
| 2008/0255584 A1* | 10/2008 | Beverland et al. ............ 606/130 |
| 2008/0287962 A1 | 11/2008 | Dick et al. |
| 2008/0294265 A1 | 11/2008 | Warkentine et al. |
| 2008/0306558 A1* | 12/2008 | Hakki ........................ 606/86 R |
| 2011/0243416 A1* | 10/2011 | Gregory et al. ................ 382/131 |
| 2013/0085723 A1* | 4/2013 | Chabanas et al. ................. 703/1 |

* cited by examiner

METHOD FOR PLANNING POSITIONING OF A BALL JOINT PROSTHESIS

This application is a national phase of International Application No. PCT/EP2011/050735 filed Jan. 20, 2011 and published in the English language.

The present invention relates to a method for planning the positioning of a ball joint prosthesis, on the basis of the position of at least one point lying on the rim of the joint socket. The present invention is in particular directed to a method for planning the positioning of a hip joint prosthesis on the basis of the position of at least two points lying in an anterior region of the acetabular rim. The present invention is also directed to a method for optimising the positioning of a ball joint prosthesis, in particular a hip joint prosthesis. Such prostheses usually comprise a cup which is placed in the pelvic bone and a stem which is placed in the femur, wherein the ball-shaped head coupled to the stem can be moved within the cup.

Although the present invention is described in connection with hip joint surgery, the present invention can also be applied to any surgery on a ball joint, such as for example a shoulder joint.

Within hip replacement surgery, it is difficult to define an optimum cup position with regard to interference with anatomical structures. Until now, most surgeons have placed the cup according to the classical Lewinnek safe zone (40°±10° inclination, 15°±10° anteversion), disregarding the interaction between the femur and the cup implant. Emerging techniques address this problem using a so-called femur-first surgical approach.

Within such an approach, the femur is prepared in a first step and the position of the (trial) implant is then determined. Based on this knowledge, the cup implant is positioned in a way which approximately optimises the post-operative range of motion. In most of the techniques, arithmetic formulae have been developed which optimise the range of motion (ROM) according to purely implant-implant impingements under certain assumptions (for example, a fixed CCD angle, femoral tilt, etc.). This approach is described in US 2008/294265. Simulations of post-operative ROMs are described in US 2008/287962 and also in U.S. Pat. No. 5,880,976, US 2006/241405 and US 2007/066917.

A particular goal for optimum cup placement is to determine an appropriate anteversion of the cup. One suggestion by Archbold et al. (*The Relationship of the Orientation of the Transverse Acetabular Ligament and Acetablular Labrum to the Suggested Safe Zones of Cup Positioning in Total Hip Arthroplasty*. Hip International, Vol. 18, No. 1, January, 2008, pp. 1-6) is to use the transverse acetabular ligament (TAL) as an aid. It has been shown that TAL can reduce dislocations and thus functionally optimise the cup position. US 2008/0255584 also suggests using this anatomical structure for navigation purposes.

In all of the above-mentioned prior art, ROM aspects are essentially addressed and the cup position/orientation is optimised for this purpose. However, a purely ROM-orientated optimisation disregards other important biomechanical aspects. None of the approaches described above includes a systematic optimisation according to such multiple criteria. This can significantly influence the biomechanical stability of the individual artificial joint.

In addition, formula-based approaches essentially use formulae for combined anteversion, i.e. the (weighted) sum of the cup anteversion and the stem antetorsion are to have a certain value. In this case, only implant-to-implant impingement can be addressed in a generic setup. Such approaches are based on many assumptions about the implant position and disregard other influences such as the CCD angle, femoral tilt or varus-valgus deviation.

The TAL approach only considers very limited information. It could be used as an additional feature within navigation procedures, but does not in itself provide a method for functional optimisation according to different significant features.

It is an object of the present invention to provide a method for planning the positioning of a ball joint prosthesis which regards the relationship between implant, bone and other anatomical features as an important aspect within artificial joint surgery and also to provide a method for optimising the positioning of a ball joint prosthesis.

The problems above are solved by the subject-matter of independent claims 1 and 13. Dependent claims define preferred embodiments of the present invention.

According to the present invention, a method for planning the positioning of a ball joint is provided, comprising the following steps:

determining the position of at least one point lying on the rim of the joint socket;

defining a requirement for the position and/or orientation of the cup on the basis of the determined positions of the at least one point.

According to a preferred embodiment of the present invention, at least one point lies superior to the point at which the psoas tendon crosses the acetabular rim and at least one point lies inferior to the point at which the psoas tendon crosses the acetabular rim. Moreover, a threshold value can be set for the distance in a lateral direction between the rim and the cup and the determined positions of the points.

The cup of the artificial joint can be axially symmetrical, wherein a threshold value can be set for the distance between a plane which is perpendicular to the symmetric axis of the cup (e.g. the opening plane of the cup which is formed by the rim of the cup) and the determined positions of the points.

The invention provides a method for using measurements of the (anterior) alignment of the cup as a guide for placing the cup. For this purpose, points on the acetabular rim can be acquired—for example, two points which are superior and inferior to the point at which the psoas tendon crosses the acetabular rim. It is then possible to calculate how far above or below the opening plane of the cup the points lie. Alternatively, the cup alignment parameters can include information about the liner used. Restrictions on these values can for example be used to prevent an anterior overhang of the cup (i.e. the edge of the cup lying above one of the points), which can cause psoas impingements (i.e. contact between the psoas tendon and the cup), or excessive undercoverage (i.e. the edge of the cup lying significantly below the points).

The information about the anterior cup alignment can also be used to restrict the anteversion of the cup in such a way that the cup does not overhang and there is thus no psoas impingement. This essentially specifies a lower threshold value for the anteversion. The threshold value can be dependent on other parameters such as the inclination or depth of the cup, since such parameters modify the values for the anterior cup alignment. The cup anteversion can then essentially be increased until no further increase in ROM, for example according to flexion and/or internal rotation at 90° of flexion movements, is achieved. These movement directions are important within this context, since they are essentially restricted by anterior or anterior-superior impingements.

The anterior cup alignment described above can also be used as an alternative to the TAL registration described in US 2008/0255584. Similar steps can be performed for this purpose. Conversely, information about the TAL—and other functional parameters which have not been described above—can be included in the cup optimisation procedure provided by the present invention.

According to the present invention, other requirements for the position and/or the orientation of the cup are defined in addition to the anterior alignment requirement. These requirements can be the range of motion (ROM) of the stem within the cup, the safe zone according to Lewinnek and/or the combined anteversion of the cup and the stem.

Moreover, a cup containment requirement is defined by the following steps:
  determining the geometric shape of the joint socket, in particular the acetabulum, and the geometric shape of the cup which is to be placed;
  defining target areas where the cup has to abut the bony structure of the joint socket, in particular the acetabulum, in order for the cup to be sufficiently fixed;
  determining actual areas of the cup which will abut the bony structure of the joint socket, in particular the acetabulum, when the cup is placed;
  defining a requirement for the position and/or orientation of the cup on the basis of the position and/or size of the target areas and/or actual areas.

According to a preferred embodiment, at least one target region is predefined on the surface of the cup facing the bone and/or is defined on the basis of the anatomical structure of the patient.

Moreover, at least one target region can be defined according to its anatomical orientation in relation to the acetabulum. At least one target region can be defined on the surface of the cup where the cup will abut on the iliac region of the acetabulum and at least one target region can be defined on the surface of the cup where the cup will abut on the ischial region of the acetabulum. Additionally, at least one target region may be defined on the surface of the cup where the cup will abut on the pubic region of the acetabulum.

The method for calculating cup containment can, for example follow the following procedure. In a first step, specific areas of the cup implant are determined in order to measure containment. These areas represent the parts of the implant which have to be covered by the acetabular bone in order to ensure a good fixation of the cup (especially in the case of press-fit cups). Bone contact in two to three sectors around the acetabular edge in the iliac, ischial, and pubic area is essentially necessary in order to achieve proper pinching and therefore a good fixation for the cup. The above-mentioned areas will therefore have to reflect these characteristics. A minimum value can be set for the size of each area, which can be calculated as fixed sectors of the cup which are adjusted to the given anatomical structures, for example according to the bony structure of the rim, or by using fixed relationships with respect to the pelvic co-ordinate system. On the basis of the 3D structure of the acetabulum, which has already been acquired by the navigation system, the cup containment is then calculated as the relative (percentage) area of the sectors which is covered by the acetabular bone. Additional values, in particular minimum values, can also be set, such as for example an overall coverage value (for example a mean value of the coverage values in the iliac, ischial and the pubic area) or a value for the coverage of the acetabular bone by the cup, and can be used as additional parameters for optimising the cup. For an interactive assessment of containment, the areas can be graphically shown to the user.

The present invention further provides a method for optimising the positioning of a ball joint prosthesis comprising the following steps:
  defining at least one requirement for the position and/or orientation of the cup;
  calculating an optimum position and/or orientation of the cup on the basis of all the defined requirements being fulfilled.

For calculating an optimum position and/or orientation of the cup, at least one parameter can be defined, such as one or more translational degrees of freedom of the cup, which may be oriented in a medial/lateral direction, in a caudal/cranial direction or in an anterior/posterior direction. Up to three rotational degrees of freedom on the cup may be recognized as well. Since such an optimisation procedure is almost impossible to perform completely manually, the optimisation process can be automatically performed by a computer, wherein calculating an optimum position involves iterative algorithms and/or algorithms employing brute-force techniques.

The invention further provides methods for calculating the optimisation criteria for individual biomechanical features such as cup alignment and containment and shows how they can be used to optimise the position of the cup. It also provides a method for combining the individual parameters to form an overall optimisation criterion which accordingly requires that all the individual features essentially be kept within an intended range, thereby guaranteeing a proper clinical outcome.

The invention also provides methods for combining multiple features—including ROM simulation steps, alignment parameters and cup coverage values—into a strategy for optimising the position of the cup implant, when the position of the femoral implant is known and information has been acquired about the anatomy on the femoral side and the acetabular side. This information will be visualised during the planning/navigation steps in order to find the optimum position of the cup.

The invention also provides a method for systematically integrating relevant individual features to form an optimisation criterion which can be automatically optimised using an appropriate optimisation algorithm. This can be a brute-force optimisation or an iterative approach (for example Levenberg-Marquardt or trust region algorithms). On the basis of this approach, a consequent optimisation can be achieved which addresses the complex relationships between the different parameters included in the optimisation criterion. the stem.

The invention can employ a navigation system for hip replacement surgery which acquires all the relevant anatomical information about the pelvis and the femur. This includes information about the co-ordinate systems (for example the pelvic planes, mechanical axis and left-right direction of the femur) and also the anatomy of the structures which are relevant to proper post-operative functioning of the joint (for example the bony anatomy of the acetabulum and the bony anatomy of the proximal femur after the femoral head has been resected). This information can be acquired before surgery, for example using known imaging techniques, or it can also be acquired intra-operatively by palpating anatomical landmarks by means of the navigation system, for example using a pointer. All the relevant information about the implants being used also has to be provided. This can include the 3D geometry of the implants and the intra-operatively determined position of the femoral (trial) implant, once the femur has been prepared. On the basis of the sum of this information, it is possible to calculate the individual functional parameters and combine them to form an overall optimisation criterion. Optimisation can be performed for different sets of parameters. A complete optimisation including six degrees of freedom (or five for rotationally symmetrical implants) can for example be performed. Alternatively, optimisation can be restricted to two degrees of freedom (inclination/anteversion) or three degrees of freedom (inclination/anteversion/depth) by assuming a fixed position in the remaining, translational degrees of freedom.

In a first step, established parameters for positioning the cup can be determined, such as the inclination and anteversion and the ROM for specific motion directions (for example, flexion, internal rotation at 90° of flexion and external rotation). These parameters are used to address the established requirements for positioning the cup implant with computer assistance. The ROM analysis can include implant-only impingement and combined bone/implant impingement. For 2D optimisation (inclination/anteversion) in particular, the bony impingement can be used as a limiting factor, since modifications to the implant orientation cannot enhance the ROM beyond the restrictions imposed by the bony structures. In general, bony impingements can be used to restrict the search space for proper cup position/orientation. It basically makes sense to vary the orientation of the cup as long as implant impingement dominates relevant restrictions on ROM In order to automatically optimise the cup position, an appropriate optimisation criterion can be calculated which combines all of the individual parameters (requirements) to form an overall assessment of the cup position. Within the framework of this invention, the main goal is to achieve an appropriate result for all the functional parameters. In a first step, an intended range can be determined for each parameter. Ideally, a suitable position of the cup is found if (almost) all of the functional parameters (requirements) remain within their intended ranges. The overall optimisation criterion can be calculated as a multiplicative combination of Heaviside functions which are "1" within the intended range and "0" outside the intended range. In general, this criterion would be too harsh as it would not allow any other variation within or outside the intended range. Such a function would also not enable an iterative optimisation algorithm to always find a suitable optimum and would not find an optimum when the intended ranges cannot all be met simultaneously.

It is therefore better to provide a fuzzy criterion for the individual parameters (requirements). This can be achieved for example using sigmoid-like functions (for example implemented using arctan functions). There is then a smooth transition zone between the inside and outside of the intended range. A threshold value and a saturation value are to be provided for this purpose. Above the saturation value, the parameter value will only have a very limited influence on the optimisation criterion. Below the threshold value, the selected pose will be drastically reduced, to reflect the fact that it should be almost prohibited to leave the intended range. The overall optimisation criterion can again be calculated as a multiplicative combination of the individual parameter (requirement) criteria. If the values do not reach zero, this can be converted into an additive combination by taking the logarithm of the individual parameter functions. For this purpose, the sigmoid-like functions can be modified in such a way that they do not (asymptotically) reach the value zero. (Additive) weightings can be used to modify the influence of individual parameters. This in particular enables a focus to be placed on certain parameters, especially when not all the intended ranges can be achieved.

Moreover, it is possible to set an upper and a lower threshold for a criterion, wherein for a certain parameter, a value between the upper and the lower threshold is allowed and a value below the lower threshold above the upper threshold is not allowed.

The automatic optimisation process can be performed using standard algorithms, including brute-force techniques or iterative algorithms (for example Levenberg-Marquardt or trust region algorithms). As already mentioned, it is possible to consider different sets of parameters, for example two degrees of freedom (inclination/anteversion), three degrees of freedom (inclination/anteversion/depth) or five degrees of freedom (or six, including all translational degrees of freedom).

Values for intended ranges of functional parameters may be provided, realized by sigmoid-like functions or multiplicative combinations of sigmoid-like functions. These criteria may be transferred into additive combinations by taking logarithms, for example, as long as these functions are non-zero. Moreover, these criteria may be weighted and restrictions for at least one search space according to dominance of bony/prosthetic impingements may be set. Information about those requirements can be collected by means of navigation systems, pre-operative data and/or anatomical or statistical relationships.

A good visual representation of the functional parameters helps the cup position to be conclusively assessed by the surgeon. This also enables a given cup position to be manually (fine-)adjusted according to the calculated functional parameters in specific situations, for example in the case of abnormal anatomies. In these cases, the initial optimisation can lead to a good initial cup position which can then be fine-adjusted. Values which are outside an intended range can be shown highlighted in order to facilitate assessment.

In summary, the present invention can take into account the following aspects:
  planning the cup according to alignment information, for example anterior alignment information;
  calculating cup containment as a value which represents the percentage of cup coverage by the acetabular bone in the areas which are most important to cup pinching;
  forming an overall optimisation criterion in order to find an optimum implant position, which combines multiple functional parameters in such a way that (almost) all the parameters are fulfilled at the same time;
  forming a strategy for using restrictions according to bony impingements to reduce the search range for calculating an optimum cup position.

DETAILED DESCRIPTION

Figure 1:
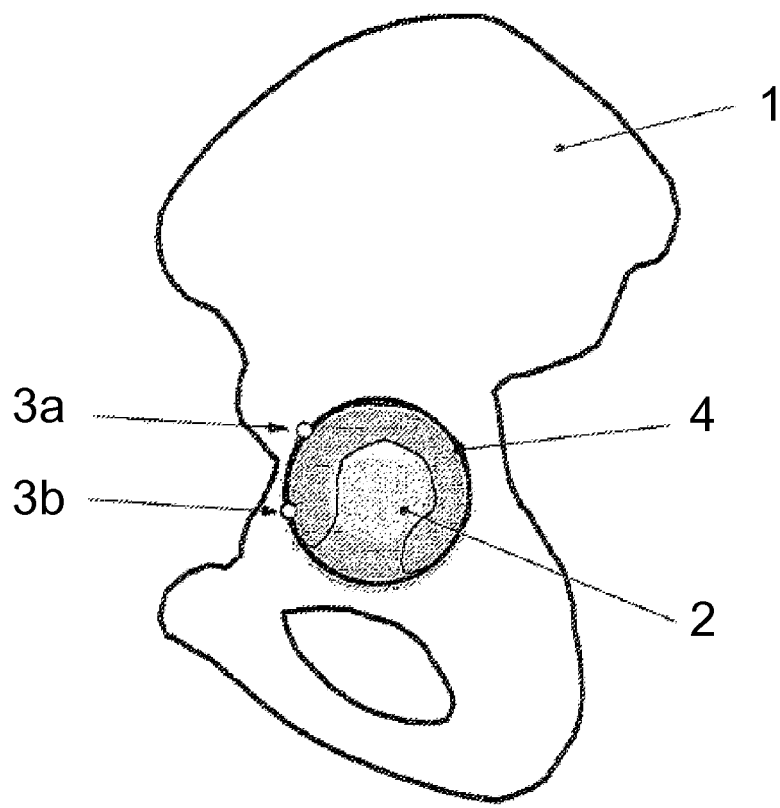
FIG. 1 shows a human pelvis and an acetabulum comprising a rim.

FIG. 1 shows a human pelvis 1 and an acetabulum 2 comprising a rim 4, wherein one point 3a lies superior to the point at which the psoas tendon crosses the acetabular rim 4, and another point 3b lies inferior to the point at which the psoas tendon crosses the acetabular rim 4. The requirement with respect to positioning the cup can be based on the position of the points 3a and 3b relative to the rim of the cup. Each of the points 3a and 3b shown in FIG. 1 is also arranged on protrusions of the acetabular rim, making it easier to palpate the points 3a and 3b.

Figure 2:
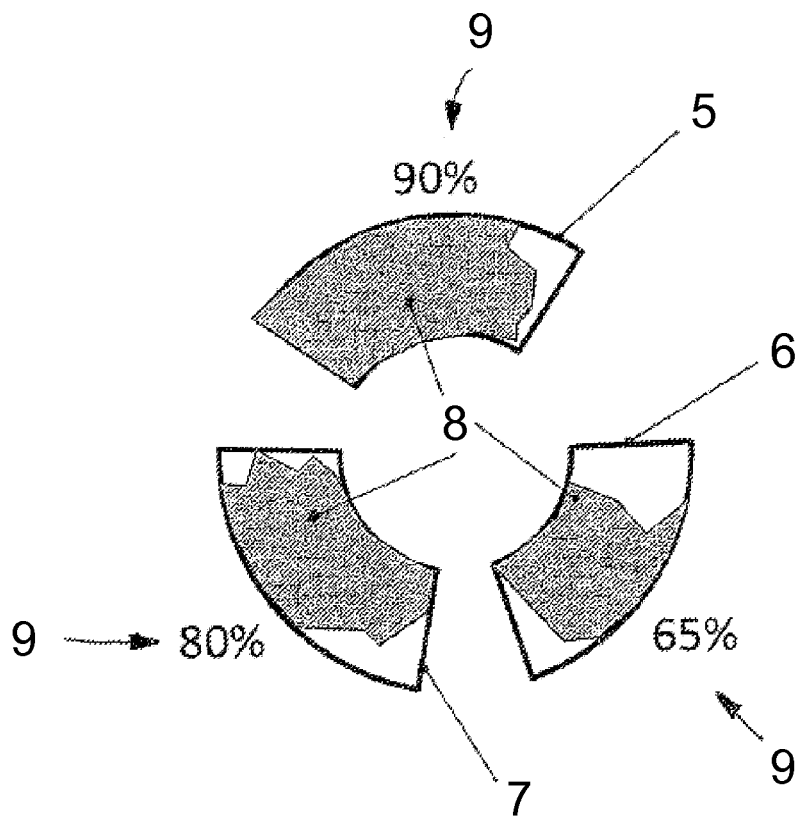
FIG. 2 shows a preferred embodiment of visualising the containment of the cup within the acetabulum.

FIG. 2 shows a preferred embodiment of visualising the containment of the cup within the acetabulum. Sectors 5, 6 and 7 which have been pre-defined on the cup for the iliac, ischial and pubic area are shown, wherein for each sector 5, 6 and 7, areas 8 are indicated which denote areas where the bony structure of the acetabulum abuts the cup. Coverage in each sector 5, 6 and 7 is also indicated as a relative value for each pre-defined sector 5, 6 and 7.

A preferred embodiment of the present invention essentially focuses on the anterior cup alignment and range of motion (ROM). This strategy essentially applies to a femur-first approach which includes determining the trial stem position (for example during broaching) and acquiring bony structures (the femur and pelvis) which are relevant to bony impingement. The preferred embodiment may comprise one or more of the following steps:

1. As a first major requirement, it is appropriate to guarantee that the cup does not overhang at the anterior rim, in order to prevent psoas impingement. This can be tested by comparing the opening plane of the cup with two points on the anterior rim (for example, points on the rim which lie directly superior and inferior to the psoas tendon, as shown in FIG. 1). The opening plane should not exceed these two points.
2. An appropriate inclination value (or range of inclination values) is determined.
3. Starting from an alignment of the cup in direct contact with the anterior rim points, the anteversion of the cup is increased (for example while maintaining a fixed inclination) until the bony impingement dominates the ROM of the joint, i.e. such that bony impingement occurs before prosthetic impingement. In particular, flexion and internal rotation at 90° of flexion should be checked, since these movement directions essentially relate to anterior impingement. The ranges of anteversion values (or pairs of inclination/anteversion values) are candidates for an optimum cup position, since the ROM cannot be enhanced beyond the bony restrictions unless bony structures are removed at the anterior slide of the rim.
4. The optimum cup position can be determined within this range by applying other parameters, for example containment, or balancing ROM values. In particular, the ROM directions relating to the anterior impingement (for example flexion and internal rotation at 90° flexion) and posterior impingement (for example external rotation at 0° flexion) could be balanced.

This approach is based on the following rationale:
Psoas impingement is to be avoided.
The anteversion of the cup is not to be increased beyond the bony ROM restrictions on the anterior side, since the ROM directions which are relevant to anterior impingement (for example flexion and internal rotation at 90° flexion) cannot be further improved, and the ROM directions which are relevant to posterior impingement (for example external rotation at 0° flexion) would be compromised. Thus, it does not make sense to increase the anteversion any further (except for minor reasons, for example in order to prevent further wear caused by posterior sub-luxations).

In most cases, it seems that the posterior impingements (for example external rotation at 0° flexion) are dominated by prosthetic impingements, unless there are osteophytes at the posterior rim.

On the anterior side, the balance between anterior alignment and depth medialisation and/or lateralisation determines whether the bony impingement or prosthetic impingement dominates. This observation is used in modification E (see below).

This approach essentially applies to optimising the cup orientation when a fixed (translational) position of the cup is given. This restriction can be eased, as described in modification D (see below).

Various modifications can be made to the approach, as described below.

A. Candidate ranges for the inclination/anteversion (and possibly also depth values) could be determined within a lower scale. The final ranges could be estimated by interpolating the results within the lower scale.
B. The limits on anterior alignment and the requirement that bony impingements not dominate need not be that strict. In particular, the requirements can be eased in the case of specific anatomies which do not allow both requirements to be completely fulfilled.
C. Following modification B, the anterior alignment information can also be used to determine how much bone (for example osteophytes) has to be removed on the anterior side for a certain range of motion to be achieved.
D. It is also possible to determine whether osteophytes should be removed on the posterior rim, for example if the bony impingement rather than the prosthetic impingement dominates on the posterior side.
E. The position of the cup (for example its depth, medialisation and/or lateralisation) can be used as an additional parameter in the optimisation procedure described. This can for example address the balance between bony/prosthetic impingements and alignment on the anterior side.
F. Statistical estimates could be used in order for example to assess the points at which prosthetic and bony impingements dominate. This could avoid the need to acquire points on the femur or other information.
G. The anteversion value could also be adjusted by the surgeon, using displays of the most relevant parameters provided by the navigation system. A slider could for example be used which allows the anteversion value to be adjusted, while the balance between the ROM values for anterior and posterior impingements is simultaneously shown.

The invention claimed is:

1. A processor-implemented method for planning the positioning of a hip ball joint prosthesis, the method comprising:
receiving, at a processor and from one of a surgical navigation system and a pre-surgery imaging system, positions of at least two points lying in an anterior region of an acetabular rim;
determining, via the processor, at least one of:
a position of a prosthetic cup, and
an orientation of the prosthetic cup,
based on the received positions of the at least two points, wherein a threshold value is set for a distance between a rim of the prosthetic cup and the at least two points; and
sending, from the processor, a hip ball joint prosthesis positioning plan including at least one of the position of the prosthetic cup and the orientation of the prosthetic cup.

2. The method according to claim 1, wherein at least one of the at least two points corresponds to a location superior to a point at which a psoas tendon crosses the acetabular rim, and at least one other of the at least two points corresponds to a location inferior to a point at which the psoas tendon crosses the acetabular rim.

3. The method according to claim 1, wherein the prosthetic cup is axially symmetrical and a threshold value is set for the distance between:

a plane which is perpendicular to the symmetry axis of the cup; and the received positions of the at least two points.

4. The method according to claim 1, wherein the determining is further based upon at least one of the following:
- a range of motion (ROM) of a prosthetic stem within the prosthetic cup;
- a safe zone according to Lewinnek; and/or
- an anteversion of a combination of the prosthetic cup and the prosthetic stem.

5. The method according to claim 1, wherein the determining comprises the following steps:
- determining the geometric shape of the acetabulum, and the geometric shape of the prosthetic cup which is to be placed;
- defining target locations at which the prosthetic cup abuts the bony structure of the acetabulum for the prosthetic cup to be sufficiently fixed;
- determining actual locations at which the prosthetic cup will abut the bony structure of the acetabulum when the prosthetic cup is placed; and
- defining a requirement for at least one of the position of the prosthetic cup and the orientation of the prosthetic cup based upon at least one of:
  - at least one of a position of the target locations and/or a size of the target locations; and/or
  - at least one of a position of the actual locations and a size of the actual locations.

6. The method according to claim 5, wherein at least one of the target locations is at least one of:
- predefined on a surface of the prosthetic cup facing the bone; and
- based upon an anatomical structure of a patient.

7. The method according to claim 5, wherein at least one of the target locations is defined in an iliac region of the acetabulum, and at least one of the target locations is defined in an ischial region of the acetabulum.

8. The method according to claim 7, wherein at least one of the target locations is defined in a pubic region of the acetabulum.

9. A method for optimising the positioning of a ball joint prosthesis, the prosthesis having a stem and a cup, the method comprising:
- planning the positioning of a ball joint prosthesis using the method according to claim 1; and
- calculating at least one of an optimum position of the cup and/or an optimum orientation of the cup based upon at least one of the determined position of the cup and the determined orientation of the cup.

10. The method according to claim 9, further comprising calculating at least one of:
- a rotational degree of freedom for the cup, and
- a translational degree of freedom for the cup.

11. The method according to claim 9, wherein the calculating is automatic and includes at least one of:
- an iterative algorithm; and/or
- a brute-force algorithm.

12. The method according to claim 10, further comprising calculating an exact threshold value for at least one parameter such that a value of the at least one parameter falling below the threshold value is allowed, and a value of the at least one parameter falling above the threshold value is not allowed.

13. The method according to claim 10, wherein an interval threshold is set for at least one parameter, such that a value for the at least one parameter falling below the threshold interval is allowed, a value for the at least one parameter falling above the interval is not allowed, and a value for the at least one parameter falling within the threshold interval is allowed to an extent that decreases from the lower limit to the upper limit of the threshold interval.

14. The method according to claim 13, wherein the extent of allowance within the threshold interval varies based on a mathematical function.

15. The method according to claim 14, wherein the mathematical function is a first sigmoid-like function, the first sigmoid-like function being multiplied with a second sigmoid-like function, yielding an overall error function.

16. The method according to claim 14, wherein the mathematical function is a first sigmoid-like function, and a logarithm of the first sigmoid-like function is added to a logarithm of a second sigmoid-type function, yielding a single error function.

17. The method according to claim 16, wherein weightings are assigned to the logarithms of the sigmoid-like error functions prior to their additive combination.

18. The method according to claim 9, wherein a search space is reduced by analysing only a region in which bony/prosthetic impingements dominate the joint's range-of-motion in specified motion directions.

19. The method according to claim 10, wherein the at least one of the rotational degree of freedom and the translational degree of freedom comprises at least one of: anteversion, inclination, rotation, translation in a medial direction, translation in a lateral direction, translation in a caudal direction, translation in a cranial direction, translation in an anterior direction, and translation in a posterior direction.

* * * * *